US00PP29051P3

(12) United States Plant Patent
Tobutt et al.

(10) Patent No.: US PP29,051 P3
(45) Date of Patent: Mar. 6, 2018

(54) ***SAMBUCUS* PLANT NAMED 'SNR1292'**

(50) Latin Name: *Sambucus nigra*
Varietal Denomination: SNR1292

(71) Applicants: Kenneth Richard Tobutt, Meopham (GB); Fiona Wilson, Aylesford (GB)

(72) Inventors: Kenneth Richard Tobutt, Meopham (GB); Fiona Wilson, Aylesford (GB)

( * ) Notice: Subject to any disclaimer, the term of this patent is extended or adjusted under 35 U.S.C. 154(b) by 16 days.

(21) Appl. No.: 14/998,769

(22) Filed: Feb. 10, 2016

(65) Prior Publication Data

US 2017/0231134 P1 Aug. 10, 2017

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Keith O Robinson
(74) *Attorney, Agent, or Firm* — Cassandra Bright

(57) ABSTRACT

A new and distinct *Sambucus* cultivar named 'SNR1292' is disclosed, characterized by a distinctly fastigiated plant habit. Foliage is very dark, turning black with maturity. The new variety is a *Sambucus* normally produced as an outdoor garden or container plant.

2 Drawing Sheets

Latin name of the genus and species: *Sambucus nigra.*
Variety denomination: 'SNR1292'.

BACKGROUND OF THE INVENTION

The new cultivar is product of a planned breeding program conducted by the inventors, Kenneth Tobutt and Fiona Wilson in Kent, United Kingom. The objective of the breeding program was to produce new *Sambucus nigra* varieties similar to the known variety 'Eva', with a compact plant form. The crossing resulting in this new variety was made during 2005.

The seed parent is the patented commercial variety known as *Sambucus* 'Eva' U.S. Plant Pat. No. 15,575. The pollen parent is an unpatented, unnamed proprietary seedling of *Sambucus nigra*. The new variety was selected during 2006 by the inventor in a group of seedlings resulting from the 2005 crossing, in a seedling trial field in Kent, UK.

Asexual reproduction of the new cultivar was performed by softwood cuttings. This was first performed at a nursery in Kent, United Kingdom in Summer of 2007 and has shown that the unique features of this cultivar are stable and reproduced true to type in 3 successive generations.

SUMMARY OF THE INVENTION

The cultivar 'SNR1292' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SNR1292' These characteristics in combination distinguish 'SNR1292' as a new and distinct *Sambucus* cultivar:

1. Fastigiate to columnar plant habit.
2. Dark, dissected foliage.
3. Inflorescences tinged pink.

PARENTAL COMPARISON

Plants of the new cultivar 'SNR1292' are similar to plants of the seed parent in most horticultural characteristics, however plants of the new cultivar 'SNR1292' differ in the following;

1. The new variety has a fastigiated plant habit, the seed parent variety has an outwardly spreading plant habit.
2. The new variety is dwarf in plant habit, reaching a shorter height than the seed parent.

Plants of the new cultivar 'SNR1292' are similar to plants of the pollen parent in most horticultural characteristics, however plants of the new cultivar 'SNR1292' differ in the following;

1. The new variety has a fastigiated plant habit, the pollen parent variety has an outwardly spreading plant habit.
2. The new variety is dwarf in plant habit, reaching a shorter height than the pollen parent.

COMMERCIAL COMPARISON

Plants of the new cultivar 'SNR1292' are comparable to the patented commercial variety *Sambucus* 'EIFFEL1', U.S. Plant Pat. No. 23,633. The two *Sambucus* varieties are similar in most horticultural characteristics; however, the new variety 'SNR1292' differs in the following:

1. Leaf color of the new variety is darker, and completely black, whereas the comparator foliage turns a greenish color, flushed with Greyed-Purple.

BRIEF DESCRIPTION OF THE PHOTOGRAPHS

Figure 1:
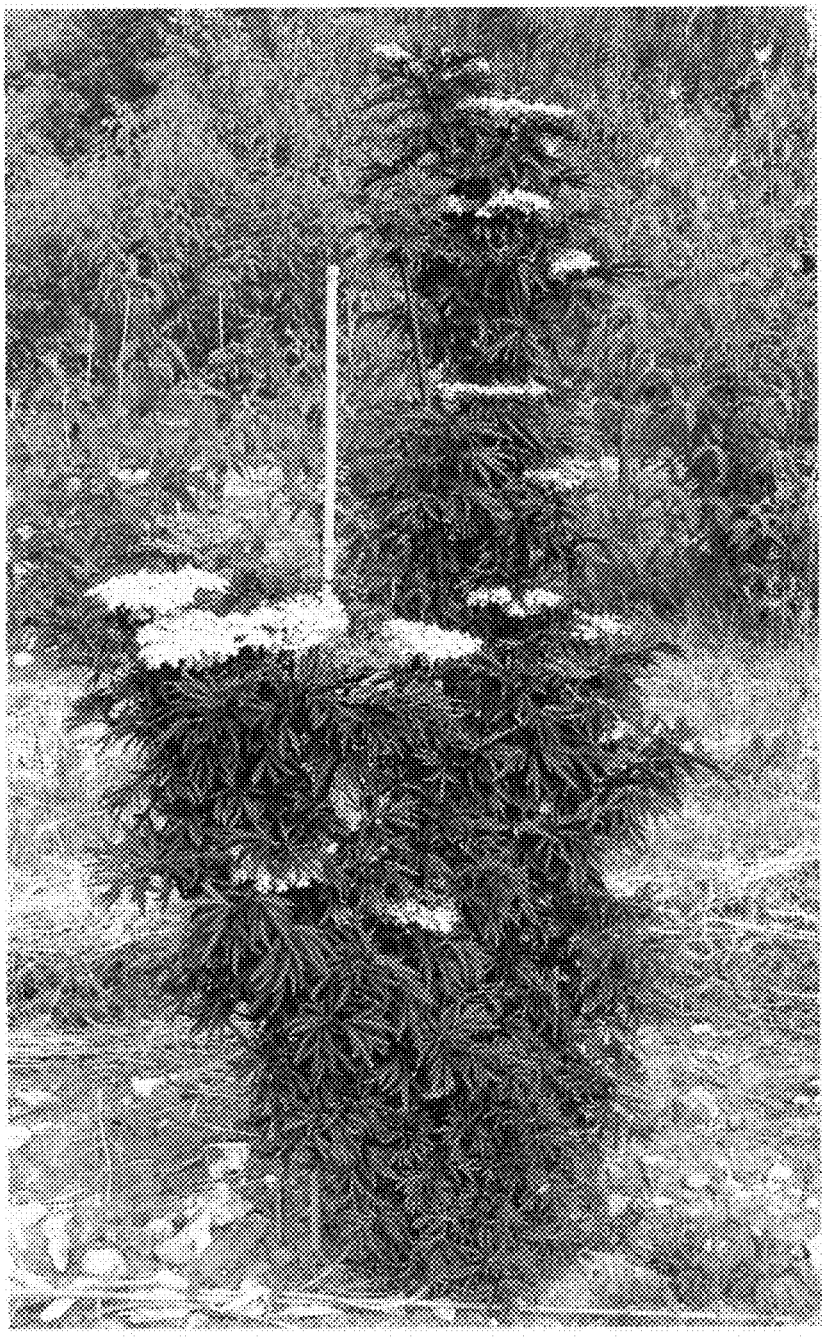

The accompanying photograph in FIG. 1 illustrates in full color a typical plant of 'SNR1292' grown outdoors, in the ground. Age of the plant photographed is approximately 6 years old from a rooted cutting.

Figure 2:
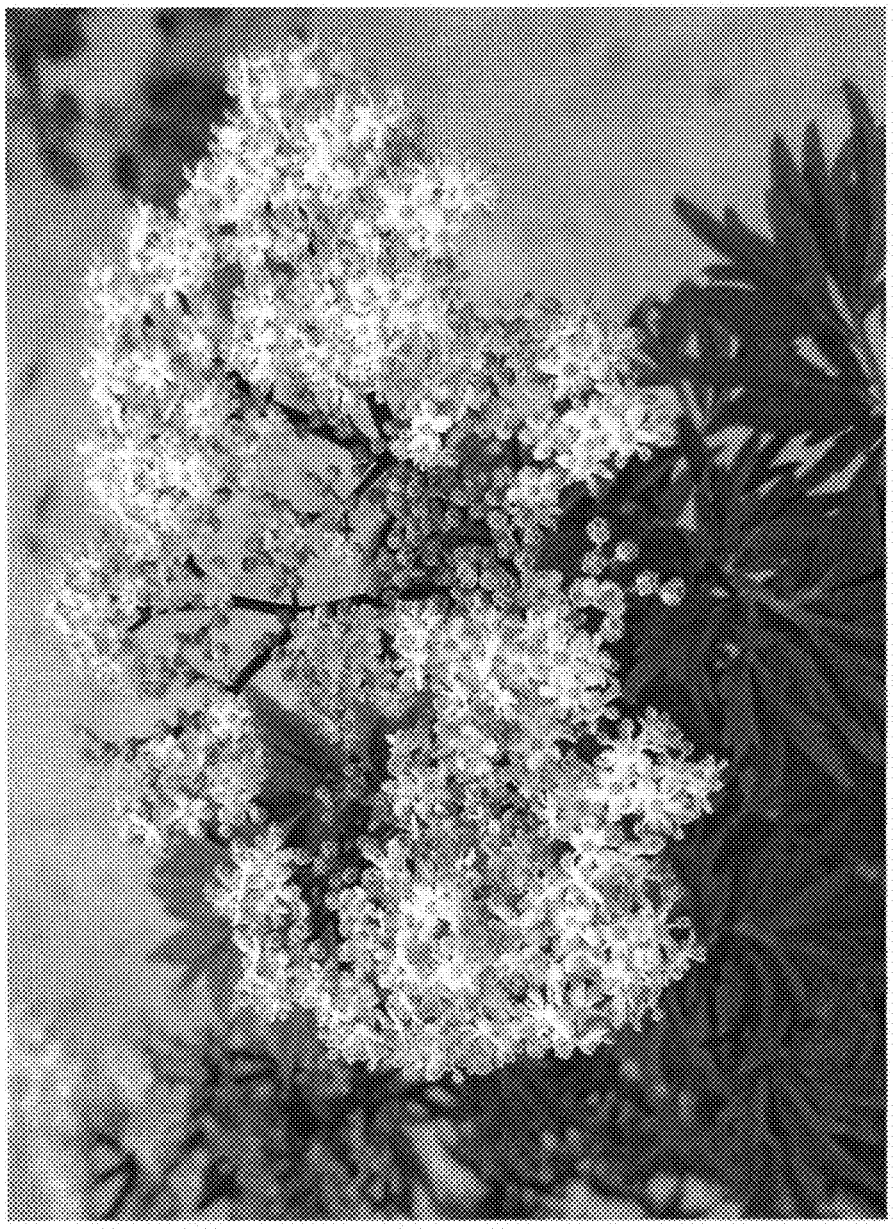

FIG. 2 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'SNR1292' plants grown in March in a poly greenhouse, in Grand Haven, Mich. USA. The growing temperature ranged from 18° C. to 27° C. during the day and from 5° C. to 10° C. during the night. General light conditions are bright, normal sunlight. Measurements and numerical values represent averages of typical plant types.

Botanical classification: *Sambucus nigra* 'SNR1292'.

PROPAGATION

Type of propagation typically used: Softwood cutting.

Time to initiate roots: 21 days at 20° C. average temperature.

Time to produce a rooted young plant: 60 days at 15-20° C. average temperature.

Root description: Moderately dense, moderately free-branching, medium thickness, non-fibrous, fleshy. Color is white, not accurately measured with The R.H.S. Chart.

PLANT

Age of plant described: 2 years from a rooted liner.

Plant type: Perennial shrub.

Container size of the plant described: 3 gallon pot.

Appropriate containers: 1, 2, 3, 5 gallon pots.

Growth habit: Fastigiate.

Overall plant shape: Columnar.

Height: Approximately 36 cm, in a 3 gallon container with has been trimmed. Mature height approximately 180 to 240 cm.

Plant spread: Approximately 35 cm in a 3 gallon container with has been trimmed. Mature width approximately 90 to 120 cm.

Growth rate: Medium fast.

Plant vigor: Good.

Characteristics of primary lateral branches:

- *Quantity.*—12.
- *Branching habit.*—Opposite, pinching not required.
- *Branch shape.*—Round.
- *Length.*—Approximately 16 cm.
- *Diameter.*—0.85 cm.
- *Color.*—RHS Greyed-Green stem color, Bark near Greyed-Brown 199B.
- *Texture.*—Main lateral branches scabrous, secondary lateral branches pubescent.
- *Stem aspect/angle.*—10-15°.
- *Strength.*—Good.
- *Internode.*—Average range 3 to 8 cm.

Leaf:

- *Arrangement.*—Opposite, compound.
- *Quantity of leaflets per leaf.*—7.
- *Average length.*—14.7 cm.
- *Average width.*—12 cm.

Leaflet:

- *Shape.*—Lanciniate.
- *Apex.*—Acute.
- *Base.*—Attenuate.
- *Margin.*—Cleft. Average Length: 5.5 cm. Average Width: 7.5 cm.
- *Texture of top surface.*—Smooth.
- *Texture of bottom surface.*—Mostly, smooth, some pubescence along veins and margin.
- *Color.*—Young foliage upper side: Base color RHS Green 141A, heavily flushed Purple 79A. Young foliage under side: Near RHS Yellow-Green 144A. Mature foliage upper side: Near RHS Black 202A. Mature foliage under side: Near RHS Greyed-Green 191A.
- *Venation.*—Type: Pinnate, semi-craspedodromous. Venation color upper side: Near RHS Greyed-Green 191A. Venation color under side: Near RHS Purple 79A.
- *Petiole.*—Length: 2.5 cm. Diameter: 2.5 mm. Color: Upper side: RHS Black 202A. Lower side: RHS Greyed-Purple 186C. Texture: Upper side: Pubescent. Lower side: Smooth, waxy.

FLOWER

Flower arrangement: Terminal umbel-like cymes. Flat polychasium.

Flower shape: Rotate.

Natural flowering season: End April/early May in Michigan.

Inflorescence height: 7 cm.

Inflorescence width: 12 cm.

Flower longevity on plant: 1-2 weeks.

Persistent or self-cleaning: Self-cleaning.

Quantity of flowers per plant: 650 to 700.

Bud:

- *Shape.*—Obovate.
- *Length.*—1.5 mm.
- *Diameter.*—2 mm.
- *Color.*—RHS Red-Purple 70A.

Flower size:

- *Diameter.*—5 mm.
- *Length.*—5 mm.
- *Depth (height).*—1 mm.

Petals:

- *Arrangement.*—Single radial whorl, not fused.
- *Petal length.*—2.5 mm.
- *Petal width.*—2 mm.
- *Quantity.*—5.
- *Texture.*—Smooth, upper and lower surfaces.
- *Apex.*—Rounded.
- *Shape.*—Oblong.
- *Base.*—Truncate.
- *Margin.*—Entire, undulate.
- *Aspect.*—Upright.

Petal color:

- *When opening.*—Upper surface: RHS White 155B, near Red-Purple 70A at apex. Lower surface: RHS White 155B, near Red-Purple 71A at apex.
- *Fully opened.*—Upper surface: RHS White 155B, near Red-Purple 70A at apex. Lower surface: RHS White 155B, near Red-Purple 71A at apex.
- *Fading to color.*—Upper and lower: RHS White 155B.

Sepals:

- *Quantity per flower.*—5.
- *Arrangement.*—Single flat whorl.
- *Shape.*—Deltate.
- *Length.*—Less than 1 mm.

*Width*.—Less than 1 mm.
*Apex*.—Acute.
*Base*.—Truncate.
*Margin*.—Entire.
*Texture*.—Upper: Smooth. Lower: Smooth.
*Color*.—Upper Surface: RHS Red-Purple 70A. Lower Surface: RHS Red-Purple 70A.

Calyx:
*Shape*.—Radial.
*Length*.—1 mm.
*Diameter*.—1 mm.

Peduncle:
*Length*.—3 to 6 cm.
*Diameter*.—2.5 mm.
*Angle*.—45°.
*Strength*.—Strong.
*Texture*.—Smooth.
*Color*.—RHS Greyed-Purple 187A.

Pedicel:
*Length*.—5 mm.
*Diameter*.—Less than 1 mm.
*Color*.—Near RHS Greyed-Purple 183A.
*Angle*.—15°.
*Texture*.—Smooth.
*Strength*.—Strong.

Fragrance: Light floral/citrus scent.

REPRODUCTIVE ORGANS

Stamens:
*Number*.—5.
*Filament length*.—2.5 mm.
*Filament color*.—RHS White 155C.

Anthers:
*Shape*.—Prolate.
*Length*.—Less than 1 mm.
*Color*.—RHS Red-Purple 58A.
*Pollen*.—Color: RHS Green-Yellow 1B. Quantity: Abundant.

Pistil:
*Number*.—1.
*Length*.—1 mm.
*Style*.—Length: less than 1 mm. Color: RHS White 155C.
*Stigma*.—Shape: Truncate. Color: RHS Red-Purple 58A. Ovary Color: RHS White 155C.

OTHER CHARACTERISTICS

Seeds and fruits: Not observed to date.

Disease/pest resistance: Neither resistance nor susceptibility to normal diseases and pests of *Sambucus* have been observed. Typical pests include Aphid (*Aphis sambuci*), various smites (*Eriophyidae* family), various borers (*Achatodes, Synathedon tipulformis*), Scale, Quadraspidiotus, various sap beetles (*Nitidulidae* family) and various *Thysanoptera*. Typical diseases include Anthracnose, Elder fungus (*Hyphodontia sambuci*), powdery mildew (not sure which) and *Verticillium* wilt.

Lowest temperature tolerance: At least to USDA zone 4.

Highest temperature tolerance: At least to USDA zone 9.

Garden performance: Excellent garden performance; very tolerant to rain and wind.

What is claimed is:

1. new and distinct cultivar of *Sambucus* plant named 'SNR1292' as herein illustrated and described.

* * * * *